United States Patent [19]

Steere et al.

[11] 4,230,983
[45] Oct. 28, 1980

[54] SEED VIABILITY ANALYZER

[75] Inventors: William C. Steere, Grass Lake; Stephen S. Wilson, Ann Arbor, both of Mich.

[73] Assignee: Agro Sciences, Inc., Ann Arbor, Mich.

[21] Appl. No.: 963,378

[22] Filed: Nov. 24, 1978

[51] Int. Cl.² .......................................... G01N 27/00
[52] U.S. Cl. ..................................... 324/71 R; 47/58
[58] Field of Search ............ 324/71 R, 62, 439, 65 R, 324/450; 47/58, 1.3, 56, 169

[56] References Cited

U.S. PATENT DOCUMENTS

3,852,914  12/1974  Levengood .................. 324/71 R

Primary Examiner—Michael J. Tokar
Attorney, Agent, or Firm—Krass & Young

[57] ABSTRACT

A method and apparatus for automatically analyzing seed characteristics. The seeds are placed one each in associated cells in a tray and the cells are filled with a deionized liquid such as distilled water. After a predetermined period of time, the conductivity of the resultant exudates are measured to provide a visual indication of the seed characteristics such as viability, vigor, and physical damage. In the apparatus, a probe head having a plurality of electrode pairs is placed on the tray so that each electrode pair is immersed in the exudate in each of the cells. An electrical potential is established between each electrode pair and the current flowing therebetween is sequentially scanned to automatically provide a visual indication of the exudate conductivity for each of the seeds in the tray cells. Preferably, the electrodes are first brought to the same potential to stabilize the exudate before establishing the potential difference across the electrodes which creates the current flow.

25 Claims, 9 Drawing Figures

SEED VIABILITY ANALYZER

BACKGROUND OF THE INVENTION

This invention relates to a method and apparatus for determining the characteristics of seeds prior to germination.

At present, a common method of determining seed germination (defined as growth of the embryo) consists of planting a predetermined number of seeds in light soil or wet toweling and determining the percent with radicle emergence after a fixed interval of time, usually seven days or more. This laboratory germination test is intended to indicate the field planting value of a seed sample (International Rules for Seed Testing, 1966). Some samples of seeds, however, show a marked discrepancy between laboratory germination and field emergency. Several attempts have been made in the past to develop tests that would better indicate the field emergency of seed samples such as germination tests in unsterilized soil and in compost. However, these tests are difficult to standardize and take several days to complete. See the articles by S. Matthews and W. T. Bradnock, Proc. Int. Seed Test. Ass. Vol. 32 (1967) No. 3, po. 553,563, and Hort. Res., 1968, Vol. 8 pp. 89–93. In search for a better and shorter test, these authors describe a 24 hour exudation test as a basis for predicting field performance. They report the discovery of a significant negative correlation between the field emergency of seed samples of peas and French beans and the readiness with which seeds from the samples yielded electrolytes to seed-steep water. They found that the samples that exuded electrolytes readily, as measured by the electrical conductivity of seed-steep water after 24 hours, gave low emergency counts in the field. They also found that in the case of peas a similar relation existed between emergence and the exudation of soluble carbohydrates. More recent work of this nature is reported by D. A. Perry and J. C. Harrison in Journal of Experimental Botany, Vol. 21, No. 67, pp. 504–12, May, 1970.

Various methods have been proposed heretofore for determining the germinating value of seeds, most of which destroy the test seeds. For example in U.S. Pat. No. 1,330,112-Gallardo there was proposed a method of determining the germinating value of seed by subjecting selected seeds to the action of a reagent which causes a contrasting difference in color between the fit or sound portions and the unfit or unsound portions of the seed. U.S. Pat. No. 2,921,598 to Aegidius there is disclosed an apparatus for determining the germination capacity of seed utilizing a reaction vessel in which selected grains after having been split longitudinally through the embryo are exposed to a reaction with an aqueous solution of a compound which causes a dyeing of the embryo if capable of germinating. In U.S. Pat. No. 3,530,372 - Laukien there is disclosed a method for automatically non-destructively testing plant seeds and sorting the seeds on the basis of the content of a specific substance, such as, e.g., water, oil, etc. The weight of a particular seed and the amount of the given substance contained in it are determined automatically, from which the specific content of the substance of the seed is calculated automatically, whereupon suitable seeds are selected using as the criterion whether the specific content is greater than a predescribed desired value.

Another test that has been applied to seeds over the years is the test for moisture content in storage; however, this is not a test for germination or field emergence. Electric moisture meters for indicating moisture in stored grains have been known for a number of years. One of the early electric moisture meters is disclosed in U.S. Pat. No. 1,059,099 - A. Zeleny (1913). Another apparatus of the electrical type for determining moisture in stored seeds and grains is disclosed in U.S. Pat. No. 2,825,870 - Hart. In the Yearbook of Agriculture "Seeds" (1961), Ways to Test Seeds for Moisture, Lawrence Zeleny points out at page 447 that factors other than moisture content affect the electrical properties of seed, and a more thorough understanding of these factors will be required before any appreciable increase in accuracy of electric moisture-testing methods can be expected.

The need for determining the potential viability of seeds is more clearly understood when it is realized that a seed grower may have a stock pile of several tons of seeds to be placed on the commercial market. If he finds, however, that the level of viability in this particular batch of seeds is lower than a prescribed standard germination level, set down by Government spedifications, then the entire batch of seeds has to be discarded. If however, a method is available for non-destructively separating out the non-viable seeds, then obviously a high percentage of the stock pile of seed could be saved for distribution.

U.S. Pat. No. 3,852,914 to Levengood discloses a recent development in which the viability of the seeds were predicted by contacting each individual seed with an electrode pair and measuring the electrical current passing through the seed. In such a manner, the seeds can be separated into groups according to their measured values of electrical current which correlates to their potential viability and vigor. While this method has proved to be extremely satisfactory, it, unfortunately, is extremely time consuming since each seed must be individually contacted by the electrodes.

SUMMARY OF THE INVENTION

In accordance with the present invention, seed characteristics of a plurality of seeds are effectively simultaneously determined by measuring the conductivity of their exudates. Preferably, a plurality of seeds are placed one each into a pocket or cell in a tray containing a multiplicity of cells. A deionized liquid, such as distilled water, is then placed into each of the cells to cover the seeds. The seeds are left to soak in the liquid for a predetermined period of time so that the seeds can imbibe the water and provide an exudate containing ionic constituents, hormones, enzymes, and other chemicals released by the seed during imbibition. A spaced electrode pair is then immersed into the exudate and a potential difference is established across the electrodes to cause an electrical current to flow therebetween. Preferably, the electrodes are first brought to the same potential to stabilize the exudate before a potential difference is applied between the electrodes. The current level of the exudate is measured and the seeds can be thus separated according to their measured current levels of their associated exudates.

In the apparatus, a plurality of electrode pairs project from one surface of a removable probe head board. The electrode pairs are oriented on the board such that when the board is placed on the tray, each electrode pair projects into the exudate in a corresponding cell in the tray. The current levels between each electrode pair is automatically sequentially scanned and a visual indication of the measured current levels are provided. In a preferred embodiment, each of the electrodes of each electrode pair is grounded and a voltage generator circuit provides a signal to the other electrode which begins at a ground level for a predetermined period of time and then makes the transition to a selected voltage level in the form of a DC pulse. Accordingly, more meaningful measurements are provided by first stabilizing the exudate by bringing the electrodes to the same potential before establishing a potential difference therebetween. According to another aspect of this invention, the seed pulse generator also controls the sequencing of a multiplexer whose inputs are coupled to one of the electrodes of each electrode pair.

Still another aspect of this invention is the provision of a comparator which compares the measured current levels of each seed exudate with a selectable partition current level and provides an output which decrements a downcounter which controls an LED display. Accordingly, the display indicates the number of seeds whose exudate current levels fall below the selected partition level thereby providing a visual indication of the percentage of viable seeds. Provision is also make for making a permanent record of the measured current levels for each of the seed exudates.

DESCRIPTION OF THE DRAWINGS

These and other advantages of the invention will become apparent upon reading the following specification and by reference to the drawings in which.

DESCRIPTION OF THE PREFERRED EMBODIMENT

Figure 1:
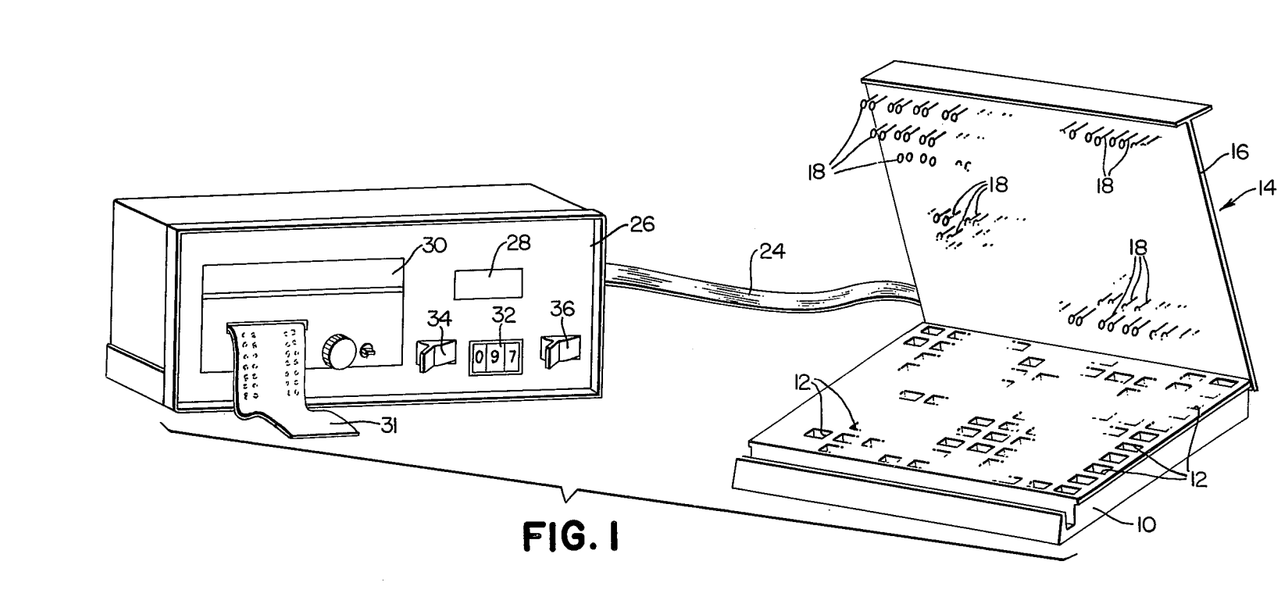
FIG. 1 is a perspective view of a preferred embodiment of this invention.
Figure 2:
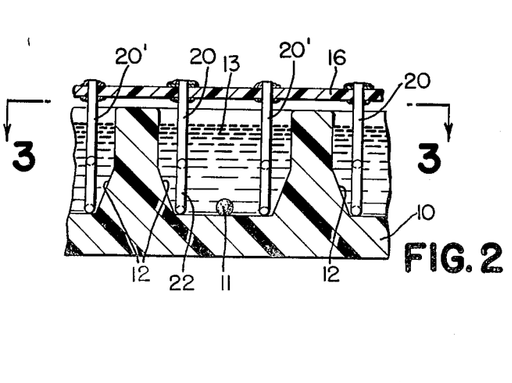
FIG. 2 is a cross sectional view illustrating an electrode pair of the probe head immersed in a seed exudate contained within a cell of an underlying tray.
Figure 3:
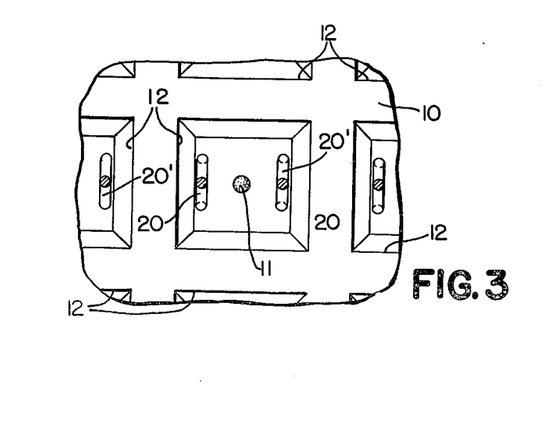
FIG. 3 is a top plan view along the lines 3—3 of FIG. 2.

Referring now to FIG. 1, there is shown a tray 10 having a plurality of pockets or cells 12 disposed in a 10×10 array on its top surface. A removable probe head 14 includes a substantially rectangular printed circuit board 16 having a plurality of spaced electrode pairs 18 projecting from its lower surface. Electrode pairs 18 are oriented on board 16 so as to correspond with the location of cells 12 in tray 10. Accordingly, when head 16 is placed on the top surface of tray 10, electrode pairs 18 engage a corresponding cell 12 as can be seen in FIG. 2. Each electrode pair 18 includes two spaced electrodes 20 and 20' preferably constructed of a stainless steel rod whose lower portions are bent into an eyelet portion 22. The electrode pairs 18 are conveniently soldered into corresponding holes in board 16, with printed conductors (not shown) on the upper surface of the board making electrical connection to the electrodes. Preferably, electrode 20 of each electrode pair 18 is connected to a common conductor which is grounded, while electrode 20' of each pair 18 is connected to a separate input of a multiplexer (see FIG. 5b) integrated circuit component which is mounted on the upper surface of board 16 as will later be more fully described.

A cable 24 provides electrical connection between probe head 14 and the electronic circuitry contained in housing 26 (FIG. 1). Housing 26 includes a light emitting diode (LED) display 28, a numerical printer 30, a partition current selector thumb wheel switch 32, mode select switch 34, and power switch 36 on its front panel.

Figure 4:
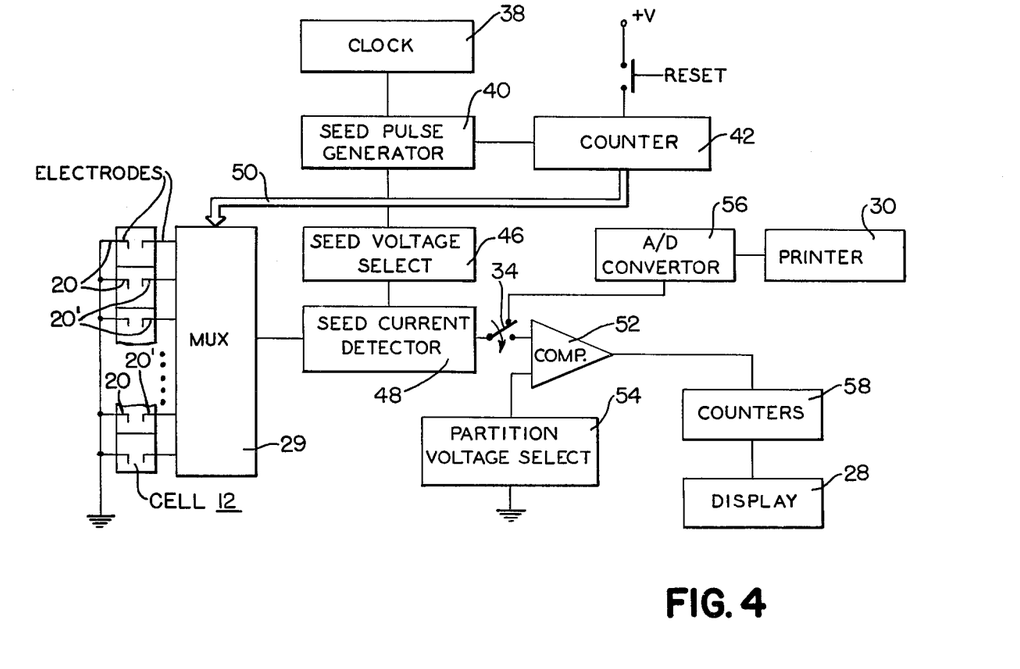
FIG. 4 is a block diagram illustrating the major components of the electrical circuitry of this invention.

A brief overview of the electrical circuitry of the present invention can be had by referring to FIG. 4 in which electrodes 20' are coupled to corresponding inputs of multiplexer 29. A clock 38 provides clock pulses to drive seed pulse generator 40 which, in turn, is coupled to a counter 42 and a current detector 48 through a voltage level selector circuit 46. Counter 42 and multiplexer 29 can be commercially available components known in the art, such as RCA component Nos. CD4040 and CD4051, respectively.

The output of counter 42 over bus lines 50 causes multiplexer 29 to sequentially connect one of its inputs to its output which is connected to current detector 48. In this embodiment, electrical current is established by applying a potential difference between electrodes 20 and 20' of each electrode pair 18. Since each electrode pair 18 is immersed in the seed exudate 13, the current level flowing between the electrodes is a function of the conductivity of the exudate. The current level for each electrode pair 18 as sensed by current detector 48 is compared by comparator 52 with a pre-selected partition current as provided by partition current selector 54. The output of comparator 52 is coupled to LED display 28 through counters 58. Alternatively, mode switch 34 can be toggled to couple detector 48 to printer 30 through analog/digital converter 56 to permanently record the measured exudate current levels for each seed. Accordingly, the exudate current levels in each of the one hundred cells 12 are automatically detected and displayed without further manual intervention.

The details of the blocks shown in FIG. 4 are illustrated more completely in FIGS. 5A-5D. For sake of clarity, dotted lines encompass the components making up the functional blocks shown in FIG. 4. Beginning with FIG. 5A, clock 38 including NAND gates 60 and 62 are coupled in a feedback relationship with capacitor Cl and resistor R1 to form an oscillator network whose frequency depends upon the RC time constant of resistor R1 and C1 as is known in the art. Clock pulses eminating from NAND gate 62 are coupled to an input of a flip-flop wired to perform the function of a one-shot multivibrator or monostable circuit 64. Monostable circuit 64 provides an output pulse of a predetermined pulse width determined by the RC network of Resistor R2 and capacitor C2. Conveniently, monostable 64 can be provided by utilizing one-half of an RCA CD 4013 flip-flop connected in the manner shown. Monostable 64 is triggered on the rising edge of the clock pulses from clock circuit 38 (see FIG. 6). The resultant output pulse from monostable 64 is coupled to the clock (CLK) input of counter 42 through gate 66. In this example counter 42 is a binary counter which is commercially available from RCA as noted above. The outputs A—F and X—Y correspond to successive bit positions, with output A corresponding to the lest significant bit, output B corresponding to the next most significant bit, etc.

Figure 5A:
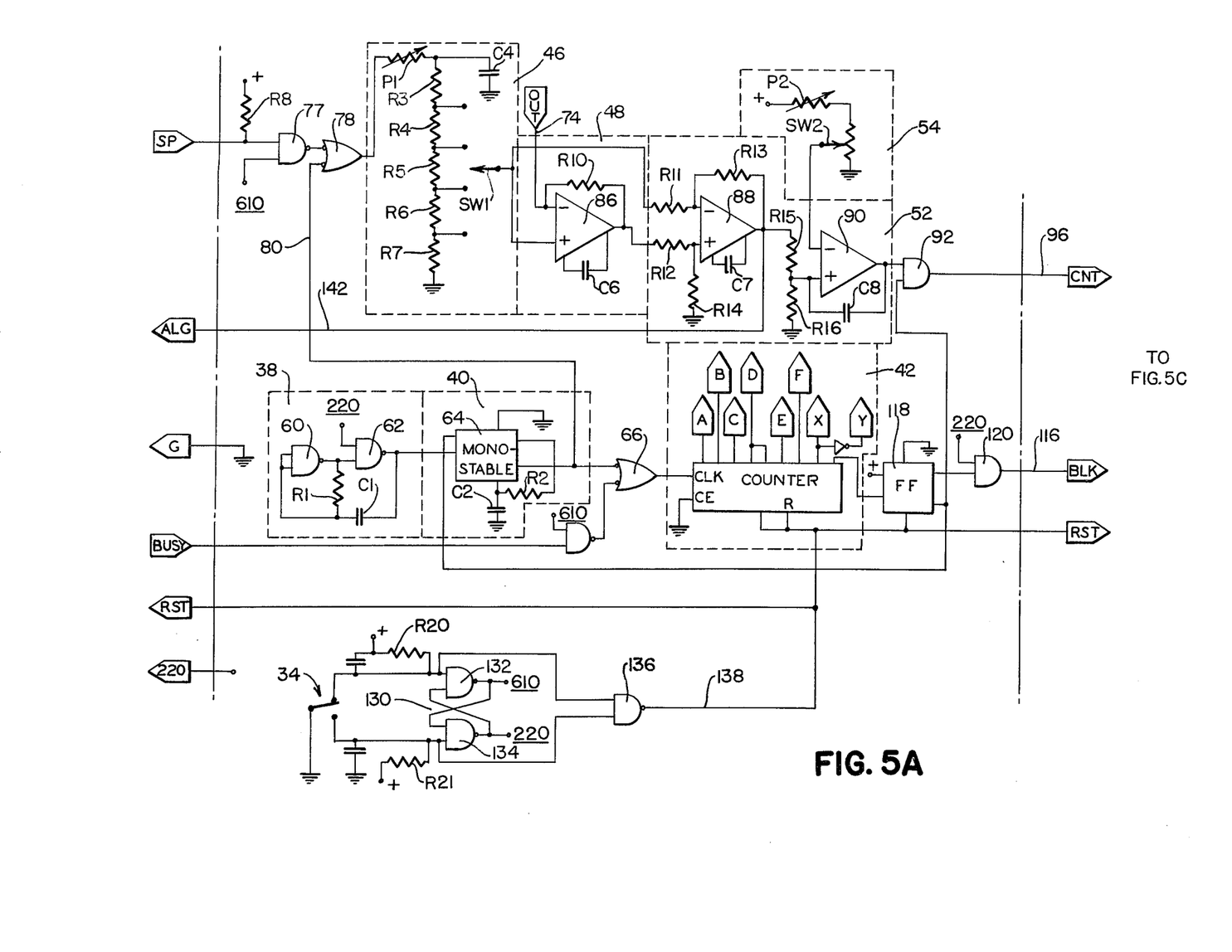
FIGS. 5A—5D comprise a schematic diagram which illustrates the details of the blocks shown in FIG. 4.
Figure 5B:
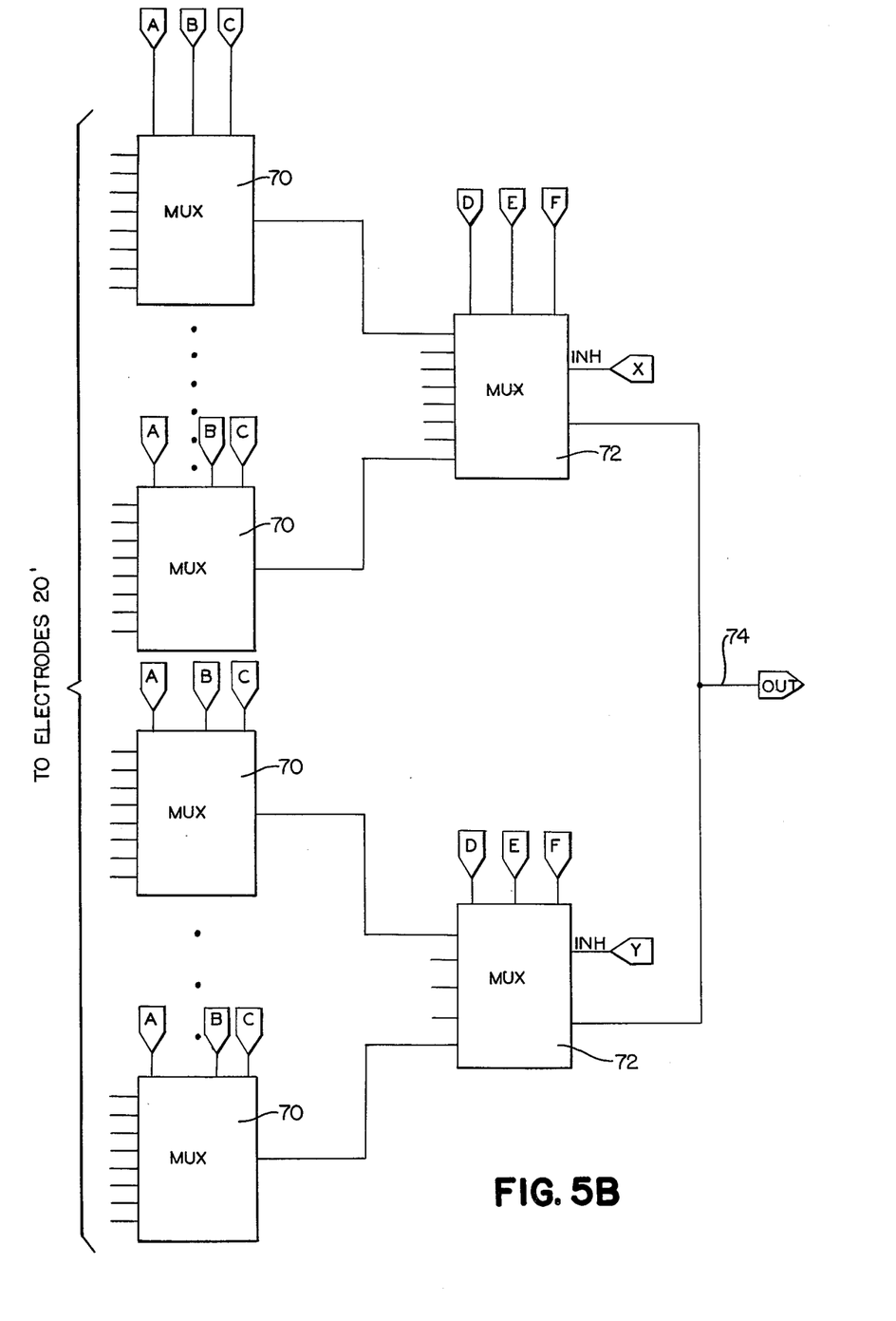

These outputs from counter 42 are coupled to sequencing inputs of multiplexers 70, 72 as shown in FIG. 5b.

Multiplexers 70, 72 are typical 8:1 devices by which one of its 8 inputs is connected to its output depending upon the signal at its sequencing input. Multiplexer 70, 72 can be those devices commercially available from RCA as noted above. In this embodiment, there are thirteen multiplexers 70 whose inputs are coupled to electrodes 20'. Accordingly, one electrode of each of the one hundred electrode pairs 18 is coupled to an input of one of the multiplexers 70 depending on the signal on lines A, B, and C. The outputs of each of the multiplexers 70 are coupled to an input of an intermediate multiplexer pair, each label with reference numeral 72. The sequencer inputs of multiplexers 72 are coupled to the D, E, and F outputs of counter 42. An inhibit signal derived from counter output X is coupled to one of the multiplexers 72, whereas another inhibit signal from counter output Y is coupled to the other multiplexer 72. The counter outputs A, B, C thus select one of the multiplexer 70 inputs and connects it with its associated output which, in turn, is coupled to the input of one of multiplexer 72. Counter outputs D, E, F selects one of multiplexer 72 inputs and connects it with its output. The inhibit signal from counter outputs X and Y will determine which multiplexer 72 output is provided on line 74 labeled OUT. Accordingly, each of the electrodes 20' are sequentially coupled to line 74 depending upon the state of counter 42 outputs A–F and X–Y. According to one aspect of this invention, multiplexers 70 and 72 are mounted on the opposite surface from electrode pairs 18 on probe head board 16 and are connected by printed circuit conductors (not shown) thereon. Accordingly, the number of conductors in connecting cable 24 are minimized. In this embodiment there only need be eleven conductors in cable 24, one each for the power, ground, A, B, C, D, E, F, X, Y, and OUT signal lines.

Referring back again to FIG. 5A, the output signal from monostable 64 is also coupled to seed voltage select circuitry 46 through gate 78 via line 80. Seed voltage select circuitry 46 includes a trim potentiometer P1 which is series connected to a voltage divider circuit comprised of resistors R3, R4, R5, R6, and R7. The amplitute of the output signal from monostable 64 is thus adjusted by the position of the wiper of switch SW1. As will be more fully discussed herein, the amplitude of the seed voltage can thus be adjusted depending upon the type of seed under test.

The seed voltage is then coupled to the seed current detector 48. The output of switch SW1 is coupled to the non-inverting input of operational amplifier 86 which is commercially available from RCA as component No. CD 3130. As is known in the art, such operational amplifiers provide a high gain and impedance so that a potential applied on one of its inputs will similarly be provided on its other input due to the feedback configuration. Accordingly, the same signal level that is applied to the noninverting input of amplifier 86 is impressed on the inverting input of amplifier 86. The inverting input of amplifier 86 is coupled to the selected electrode 20' through the multiplexing arrangement shown in FIG. 5. Accordingly, the seed voltage from generator 40 is thus coupled to the selected electrode 20'. A current path is provided between the inverting input of amplifier 86 and the output thereof through resistor R10. The voltage produced at the output of amplifier 86 is thus a function of the current passing through the selected electrode pair 18 which, in turn, is a function of the conductivity of the exudate in the particular cell 12 selected. This voltage can be expressed by the following equation:

$$V = I_s[R] + V_s$$

Where:

V equals the voltage at the output of amplifier 86;

$I_s$ is the current flowing through the particular seed exudate;

R equals the value of resistor R10; and $V_s$ is the seed voltage supplied by seed pulse generator 40.

The output of amplifier 86 is coupled to one input of a differentially connected amplifier 88. The seed voltage is coupled to the inverting input of amplifier 88 through resistor R11. Thus, the output of amplifier 88 effectively subtracts the term $V_s$ from the above equation. Accordingly, the output signal from amplifier 88 is directly proportional to the seed exudate current level.

Figure 5C:
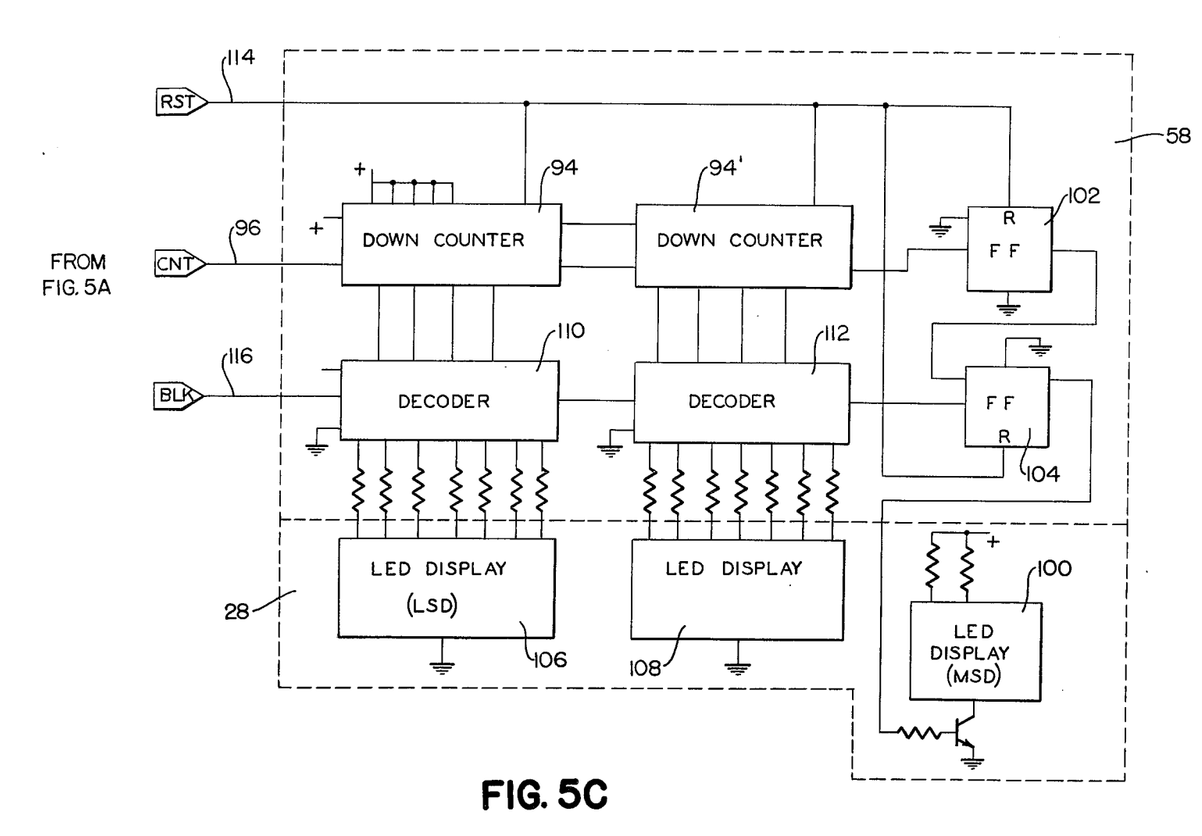

Comparator 52 includes comparator amplifier 90 to which the output of amplifier 88 is connected through resistor R15 to its noninverting input. The inverting input of amplifier 90 is coupled to the partition current level circuitry 54. Partition current selector 54 includes a trim potentiometer P2 and a manually adjustable thumbwheel pontentiometer switch SW2 represented by switch 32 on the front panel of housing 26 as shown in FIG. 1. Accordingly, the user can establish a desired partition current level against which the seed exudate current level is compared by comparator 90. If the seed exudate current level is above the partition current level, the resultant positive output of comparator 90 activates gate 92 to provide an output pulse which is connected to down counters 94 and 94' as can be seen in FIG. 5C. Down counters 94 and 94' control the activation of LED display 28. Display 28 is initially set to read 100. Accordingly, if the measured seed exudate level is above the partition level, the LED display 28 is caused to decrement. Since the partition current is selected at a level which sets the maximum acceptable seed exudate current level for the seeds under test, the display 28 will provide an indication of the percentage of tested seeds whose exudate current levels fall below this cut off. Those seeds whose exudate current levels fall below the chosen partition level will provide no output from comparator 90 which does not activate gate 92 to decrement the display 28 when mode selector switch 34 is in its LED display or 220 mode.

FIG. 5C shows the details of the counters 58 and display 28. LED display 100 provides a visual indication of the most significant digit. Since display 28 is initially reset to 100 and it is then decremented, display 100 will either be a 1 or 0. Accordingly, it is controlled by the action of the flip-flop circuits 102 and 104 whereas upon receiving the first signal from counter line 96, display 100 changes from a 1 to 0 numeral orientation. Displays 106 and 108 are similar seven segment LED displays, with display 108 providing the second most significant or tens place digit and display 106 providing the least significant or zeros place digit. Seven segment decoders 110 and 112 coupled to displays 106 and 108, respectively, are utilized as known in the art to control the activation of the various segments in the LED display. Accordingly, upon initially beginning the test run, a reset signal on line 114 causes LED display 28 to read 100 and the display is decremented for every counter pulse received on line 96. Preferably, the display 28 is blanked by a signal over line 116 emanating from flip-flop 118 (See FIG. 5A) and gate 120. Accordingly, flip-flop 118 which is coupled to the most significant digit bit place of counter 42 is not set until all of the cells have been tested. Hence, the display 28 illustrates only the final tally after all of the cells have been tested.

Referring briefly to FIG. 5A, the mode switch 34 is a three position switch normally resting in the center position. The poles of switch 34 are coupled to a latch 130 comprised of cross coupled NAND gates 132 and 134. When the wiper of switch 34 momentarily contacts one of the two poles, gate 136 provides a reset signal on line 138 to reset display 28 and other associated components such as counters, flip-flops, etc., in a manner known in the art. Depending upon the direction switch 34 is flicked, either gate 132 or gate 134 will supply an energizing output signal to selected components. The output labeled 220 is provided when switch 34 momentarily contacts its display position, with output labeled 610 provided when switch 34 momentarily contacts its printer position. The above description has assumed that latch 130 was in its display mode. When latch 130 is in its printer mode, printer 30 is activated to provide a print out on paper 31 in which each line on the paper 31 includes the number of the cell tested and its measured current level.

Figure 5D:
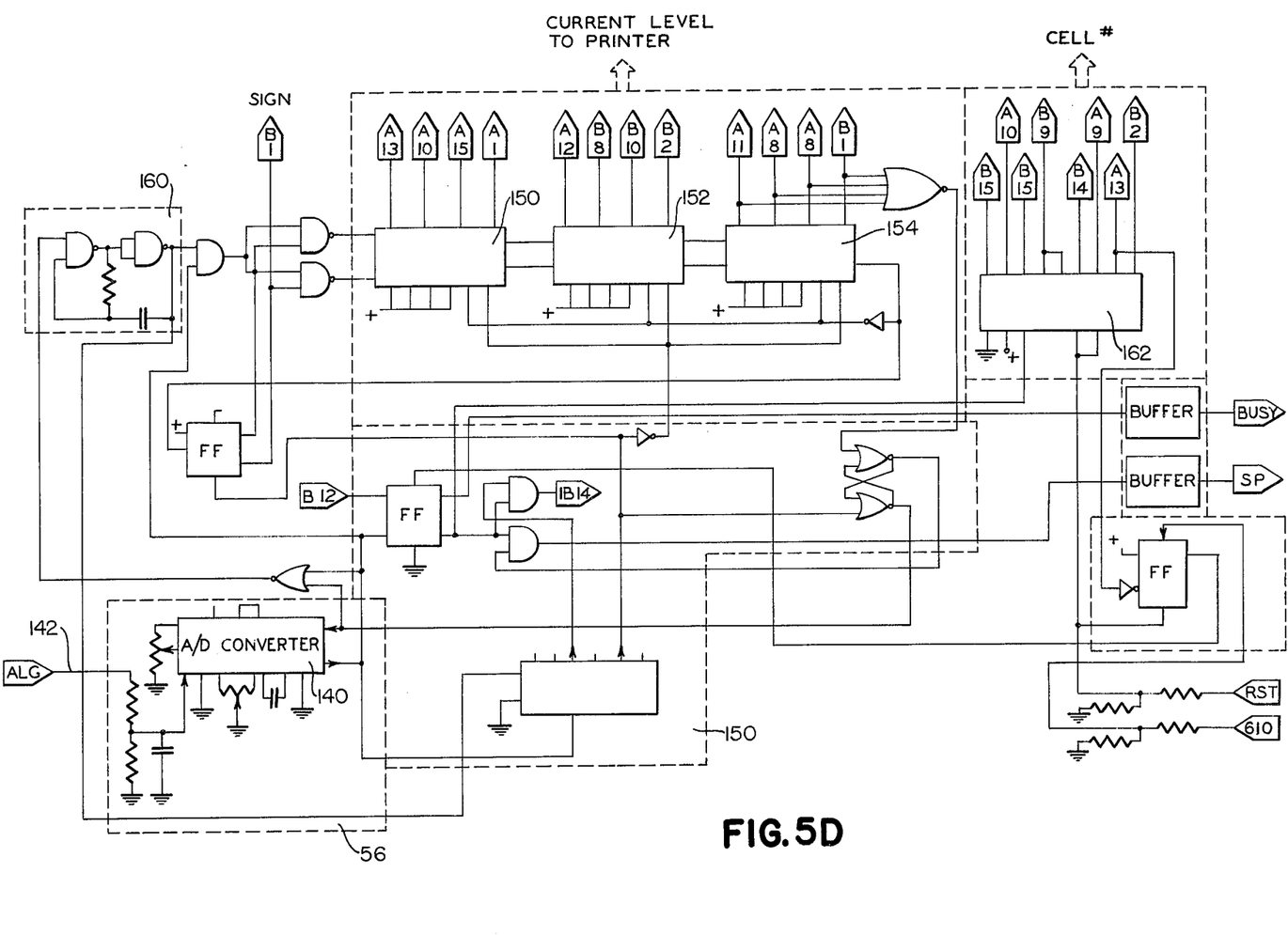

Referring now to FIG. 5D, when the printer 30 is used, the output of amplifier 88 is coupled to an analog to digital converter 140 over line 142 labeled ALG. A/D converter 140 is well known in the art and can be purchased from Motorola Semiconductors as Component No. MC1405. The operation of such converters are well known in the art, and includes circuitry 150 to control the known dual ramp operation of converter 140. Briefly, the analog representation of the seed current level is converted to a digital value by A/D converter 140. The output of converter 140 is coupled to three binary coded decimal (BCD) counters 150, 152, and 154. The outputs of counters 150-154 provide a compatible signal to printer 30 so that it can print the current level on one line of paper 31. Counters 150-154 are commercially available from RCA as Component No. CD74192. In this embodiment, printer 30 is a thermal printer distributed by Datel Corporation. An oscillator 160 provides clock pulses to synchronize the operation of the components shown in FIG. 5D. A seed pulse over line SP is provided in a similar manner as that described in connection with monostable 64 of FIG. 5A. A signal is also provided on the line labeled BUSY to indicate that the printer is activated to temporarily halt the switching to a new cell 12 for measurement. The cell number is also printed adjacent its measured current level through the action of counter 162 whose BCD outputs are also coupled to printer 30. Accordingly, as each cell exudate is measured, its cell number and current level is printed by printer 30 onto paper 131 to provide a permanent record of all of the tested seed exudates.

OPERATION

One hundred seeds are randomly selected from a seed lot whose characteristics, such as standard germination rate, are desired to be tested. Each seed 11 is placed in a separate cell 12 in tray 10. The cells 12 are then filled with a deionized liquid such as distilled water. The seeds are then left to soak for a predetermined period of time so that they can fully imbibe the water. Preferably, the seeds can be left to soak overnight for approximately 18-20 hours. Thus, the seeds will have reached the hydration phase in which hormones and enzymes and other chemicals are released into the surrounding liquid.

The seed voltage select circuitry 46 and partition current selector circuitry 54 are then utilized to select the seed pulse voltage setting and microamp partition current level according to the following table which sets out some preferred settings for a variety of seeds.

| Seed Type | Seed Voltage | Partition Current Level (microamps) |
| --- | --- | --- |
| Barley | 1.5 volts | 75 |
| Wheat | 1.5 volts | 70 |
| Sorghum | 1.5 volts | 90 |
| Cottonseed | | |
| (a) Delinted | .25 volts | 60 |
| (b) Fuzzy | .25 volts | 55 |
| Soybeans | .25 volts | 90 |
| Sunflower | .25 volts | 100 |

Figure 6:
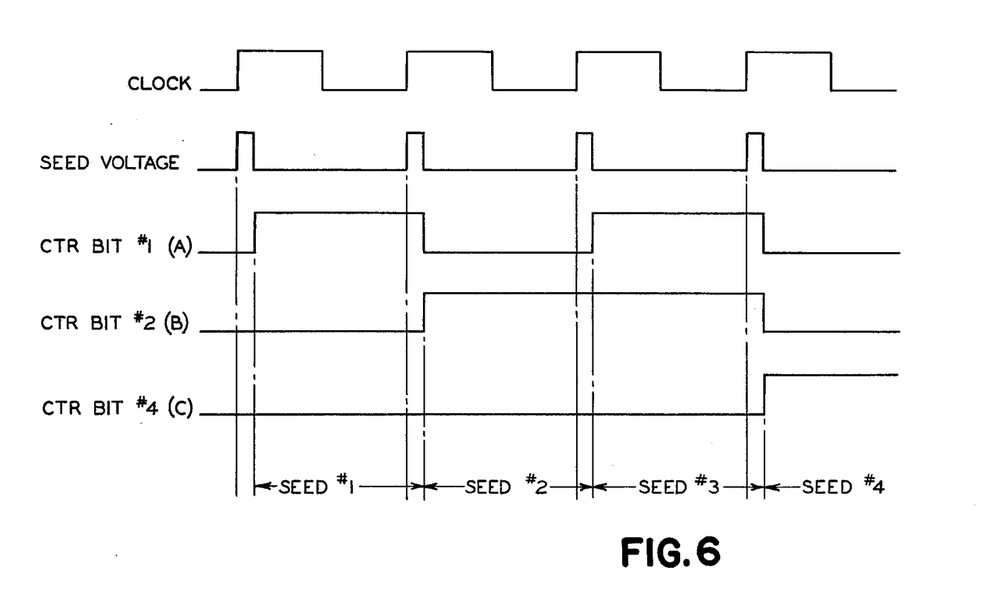
FIG. 6 is a timing chart illustrating the timing relationship of the signals from some of the components shown in FIG. 4.

Probe head 14 is then placed on top of tray 10 so that each of the electrode pairs 18 project into the seed exudate 13 of each of the cells 12 as shown in FIG. 2. Mode switch 34 is then momentarily toggled to place its wiper in either the printer (610) or LED display (220) mode position. During the toggling action, the displays, counters, flip flops, etc. are reset as described above. Assume for this example that switch 34 is placed in the LED display mode. Referring especially to FIG. 6, the rising edge of the clock pulses from clock 38 triggers monostable 64 to provide an output DC pulse whose width is substantially shorter than the clock pulse. In the preferred embodiment, the output signal from monostable 64 is a DC pulse having a HIGH level approximately 1 millisecond in width and an amplitude of about 12 volts (which can be adjusted by voltage selector circuit 46 to provide the desired setting) and a grounded LOW level signal approximately 100 milliseconds in duration. Counter 42 is incremented on the falling edge of the DC pulse from monostable 64. Accordingly, electrode 20' of the first cell 12 is connected to current detector 48. As can be seen most clearly in FIG. 5A and by reference to the timing chart in FIG. 6, the voltage applied to the selected electrode 20' (through the inverting input of amplifier 86) begins with a grounded low level signal and then changes to a DC pulse of the selected voltage level. We have discovered that more meaningful readings are obtained when the electrodes of the selected electrode pair 18 are brought to the same potential for a predetermined period of time before establishing a potential difference therebetween which initiates the current flow. Although this phenomenon is not clearly understood, it is believed that this causes the exudate to stabilize and remove residual polarization effects which could change the conductivity reading of the exudate. When the HIGH level signal is applied to electrode 20', the current flow between the electrode pair is detected by current detector 48. This current level is compared by comparator 52 with the selected partition current level. If the measured exudate current is above the partition level, the display 28 is decremented from its initial 100 setting to 99.

During the transition of the seed voltage from its HIGH level to its LOW level, counter 42 is incremented to select cell number 2 through multiplexer complex 30. Again, the electrode 20' immersed in the second cell is brought to a ground level potential during the LOW level signal from monostable 64 to stabilize the exudate solution in the second cell. When the HIGH level signal is applied to the selected electrode 20' to establish a potential difference between the electrodes of the pair, the resulting current level is measured and compared with the partition level in the manner previously described. Assume, for example, that the measured current level for cell number 2 falls below the partition level. Consequently, display 28 is not decremented since the current level for that seed exudate is acceptable. This process continues for all of the remaining cells 12 in tray 10. When the last cell has been tested, flip-flop 118 (see FIG. 5A) is activated by counter 42 to remove the blanking signal on line 116 from the display 28 so that it may show the final tally. If, for example 93 of the 100 cells tested had current levels which fall below the partition level, the display 28 will illustrate the number 93. Accordingly, the user has a reliable prediction that 93 percent of the seeds in the lot will meet the standard germination rate.

It can now be realized that the present invention provides an automatic seed analyzing system by which various characteristics of seeds can be tested. The conductivity of the seed exudates has proven to be a reliable prediction of the actual germination, vigor, and mechanical damage of the seeds. Moreover, the seeds can be separated according to their exudate conductivity levels for variety breeding purposes. For example, the seeds having the lowest exudate current levels can be separated and inbred to provide a new strain of exceptionally good characteristics.

Therefore, while this invention has been described in connection with certain examples thereof, no limitation is intended thereby except as defined in the appended claims.

The embodiments of the invention in which an exclusive property or privilege is claimed are defined as follows:

1. A method of analyzing seed characteristics comprising:
    (a) placing a plurality of seeds one each into a plurality of cells in a tray;
    (b) filling the cells with a deionized liquid;
    (c) allowing the seeds to imbibe the liquid and produce an exudate; and
    (d) sequentially measuring the conductivity of each of the seed exudates thereby providing an indication of the seed characteristic under analysis.

2. The method of claim 1 wherein step d further comprises placing a pair of spaced electrodes into each of the cells and measuring the current flow between the electrodes.

3. The method of claim 2 wherein step d further comprises the steps of initially bringing the electrodes to the same electrical potential to stabilize the exudate; and
    thereafter, applying a selected potential difference between the electrodes to create current flow therebetween.

4. The method of claim 3 wherein a DC pulse signal having a grounded LOW level is applied to one of the electrodes, with the other electrode being grounded.

5. The method of claim 4 which further comprises the step of:
    placing a board having a plurality of electrode pairs depending therefrom onto said container so that an electrode pair extends into the exudate in each of the cells.

6. The method of claim 5 which further comprises the steps of sequentially scanning each of the electrode pairs to measure the current flow therebetween.

7. The method of claim 6 which further comprises the step of displaying an indication of the measured current flow for each of the seed exudates.

8. The method of claim 7 which further comprises the steps of:
    comparing the measured current level of each seed exudate with a selected partition current level; and
    displaying the number of seeds whose associated exudate current levels does not exceed that partition level.

9. The method of claim 7 wherein the measured current levels for each seed is printed on a readable medium.

10. The method of claim 9 which further comprises the step of separating the seeds according to the measured current levels of their exudate.

11. Apparatus for automatically measuring the conductivity of a plurality of seed exudate solutions contained in a plurality of cells in a tray, said apparatus comprising;
    a board having a plurality of electrode pairs depending from one surface thereof, said electrode pairs being located on said board corresponding to the location of the cells in the tray where upon placing the board on the tray the electrode pairs extend into the exudate in each of the cells; and
    means for measuring the current flow between each of the electrode pairs to thereby provide an indication of the conductivity of the exudate in each of the cells.

12. The apparatus of claim 11 which further comprises:
    generator means for sequentially establishing an electrical potential between each of the electrode pairs.

13. The apparatus of claim 12 wherein said generator means brings the electrodes of each electrode pair to the same potential before establishing a potential difference therebetween.

14. The apparatus of claim 13 wherein one electrode of each electrode pair is grounded, and wherein said generator means provides a grounded LOW level DC pulse to the other electrode.

15. Apparatus for automatically measuring the conductivity of seed exudates contained in a multiplicity of cells in a tray, said apparatus comprising:
    a sensor board having a plurality of electrode pairs projecting from one surface thereof, each electrode pair being adapted to be immersed in the exudate contained within one of the cells;
    multiplexer means having a plurality of inputs connected to one of the electrodes of each of the electrode pairs, said multiplexer means having an output and a sequencer input for sequentially connecting one of said inputs to said output;
    clock means for providing a plurality of clock pulses;
    counter means having an input coupled to said clock means and an output coupled to the sequencer input of said multiplexer;
    current detector means coupled to the output of said multiplexer for measuring the current flow between each of said electrode pairs as they are sequentially coupled to the output of the multiplexer; and means for providing a visual indication of the exudate conductivity for each of the seed cells as sensed by said current detector means.

16. The apparatus of claim 15 which further comprises:
generator means for establishing an electrical potential between each electrode pair as each pair is coupled to the output of said multiplexer.

17. The apparatus of claim 16 wherein said generator means first brings the electrodes of each pair to the same potential for a predetermined period of time before establishing a potential difference therebetween.

18. The apparatus of claim 17 wherein one of the electrodes of each electrode pair is grounded and wherein said generator means provides a ground level signal to the other probe for a predetermined period of time and then applies a selected voltage level to the other electrode to thereby initiate current flow therebetween.

19. The apparatus of claim 18 which further comprises:
means for selecting different voltage levels for the signal from said generator means.

20. The apparatus of claim 19 wherein said current detector means comprises:
a first operational amplifier having first and second inputs and output, operative to establish the same potential at said second input when a potential is applied to said first input, and a current path between said second input and said output;
means coupling said first input of said first operational amplifier to said generator means; and means for coupling the output of said multiplexer to said second input of said operational amplifier whereby upon said selected voltage level being applied to said first input an equivalent potential is applied across the electrode pair coupled to the output of said multiplexer thereby establishing current flow in said path as a fuction of the conductivity of the exudate of the particular cell.

21. The apparatus of claim 20 which further comprises:
manually adjustable means for providig a partition current level;
comparator means for comparing said partition current level with the output of said first operational amplifier, with said comparator providing an output signal when said current from the operational amplifier is above the partition current level.

22. The apparatus of claim 21 wherein the output of said comparator is coupled to a display control means for decrementing a display upon receiving each output signal from said comparator thereby providing a visual indication of the number of seeds whose exudate current levels are below said selected partition current level.

23. The apparatus of claim 22 wherein said generator means comprises:
monostable means having an input coupled to said clock means and an output coupled to the input of said counter and to the first input of said first operational amplifier, said monostable means providing an output signal of a grounded LOW level in one sate and of a HIGH level of a given pulse width in an opposite state upon receipt of a trigger pulse for said clock means wherein the output signal of said monostable means causes said multiplexer to sequence to the next electrode pair during transition from said HIGH to LOW level, and supplies the stabilizing potential across the electrode pair, with the subsequently applied HIGH level establishing the current inducing potential between the electrodes.

24. The apparatus of claim 23 wherein said monostable means switches to its HIGH level output during the rising edge of the pulses from said clock means, and wherein said counter is incremented during the falling edge of the output signal from said monostable means.

25. The apparatus of claim 24 wherein said multiplexer is mounted on said sensor board on the opposite surface from said electrodes.

* * * * *